United States Patent
Graupe et al.

(10) Patent No.: US 7,680,531 B2
(45) Date of Patent: Mar. 16, 2010

(54) SEPARATION OF ONE OR MORE FETAL HEART COMPONENT SIGNALS FROM HEART SIGNAL INFORMATION OBTAINED FROM A PREGNANT FEMALE

(75) Inventors: Menachem H. Graupe, Mequon, WI (US); Daniel Graupe, Highland Park, IL (US); Piotr L. Suliga, Chicago, IL (US); Yunde Zhong, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 10/595,594

(22) PCT Filed: Oct. 22, 2004

(86) PCT No.: PCT/US2004/035125

§ 371 (c)(1), (2), (4) Date: Apr. 28, 2006

(87) PCT Pub. No.: WO2005/044101

PCT Pub. Date: May 19, 2005

(65) Prior Publication Data

US 2007/0066908 A1    Mar. 22, 2007

Related U.S. Application Data

(60) Provisional application No. 60/516,343, filed on Oct. 31, 2003.

(51) Int. Cl.
   *A61B 5/04* (2006.01)
(52) U.S. Cl. .................................... 600/511; 381/71.11
(58) Field of Classification Search ........................ None
   See application file for complete search history.

(56) References Cited

U.S. PATENT DOCUMENTS

| | | | | |
|---|---|---|---|---|
| 5,209,237 | A * | 5/1993 | Rosenthal | 600/511 |
| 5,704,365 | A * | 1/1998 | Albrecht et al. | 600/515 |
| 5,784,162 | A * | 7/1998 | Cabib et al. | 356/456 |
| 5,917,919 | A * | 6/1999 | Rosenthal | 381/71.11 |
| 2004/0260169 | A1 * | 12/2004 | Sternnickel | 600/409 |

FOREIGN PATENT DOCUMENTS

WO    03/028550 A2    4/2003

OTHER PUBLICATIONS

K. Reed, "Diagnosis and Treatment of Fetal Cardiac Arrhythmias," UpToDate Patient Information—Publication, Oct. 2004, 2 pp., UpToDate.com, Wellesley, MA, USA.

P. Suliga & D. Graupe, "Smart Engineering System Design: Neural Networks, Fuzzy Logic, Evolutionary Programming, Data Mining, and complex Systems," Intelligent Engineering Systems Through Artificial Neural Networks vol. 12—Book, Nov. 2002, 690-694 (6 pp.), ASME Press, New York, USA.

(Continued)

*Primary Examiner*—Carl H. Layno
*Assistant Examiner*—Jon-Eric C. Morales
(74) *Attorney, Agent, or Firm*—Robert J. Brill; Wood Phillips

(57) ABSTRACT

One or more fetal heart component signals in one example are separated from heart signal information obtained from a pregnant female based on singular value decomposition.

37 Claims, 8 Drawing Sheets

OTHER PUBLICATIONS

P. Diniz, E. Da Silva & S. Netto, Digial Signal Processing System Analysis and Design—Book, 2002, 427-441 (17 pp.), The Press Syndicate of the University of Cambridge, Cambridge, United Kingdom.

A. Oppenheim & R. Schafer, Digital Signal Processing—Book, 1975, 500-507; 528-529 (12 pp.), Prentice-Hall, Inc., Englewood Cliffs, New Jersey, USA.

A. Cichocki & S. Amari, Adaptive Blind Signal and Image Processing Learning Algorithms and Applications— Book, 2002, 243-253; 285-291 (20 pp.), John Wiley & Sons, Ltd., West Sussex, England.

D. Graupe, Time Series Analysis, Identification and Adaptive Filtering—2nd Edition—Book, 1989, 61-61; 195-206; 217-226 (26 pp.), Robert E. Krieger Publishing Co., Malabar, Florida, USA.

L. Tong, R. Liu et al., "Indeterminacy and Identifiability of Blind Identification," IEEE Transactions on Circuits and Systems, vol. 38, No. 5—Publication, May 1991, 499-509 (11 pp.), IEEE (Institute of Electrical & Electronics Engineers), USA.

D. Graupe, "Blind Adaptive Filtering of Speec from Noise of Unknown Spectrum Using a Virtual Feedback Configuration," IEEE Transactions on Speec and Audio Processing, vol. 8, No. 2—Publication, Mar. 2000, 146-158 (13 pp.), IEEE (Institute of Electrical & Electronics Engineers), USA.

D. Veselinovic & D. Graupe, "A Wavelet Transform Approach to Blind Adaptive Filtering of Speech from Unknown Noises," IEEE Transactions on Circuits and Systems-II: Analog and Digital Signal Processing, vol. 50, No. 3—Publication, Mar. 2003, 150-154 (5 pp.), IEEE (Institute of Electrical & Electronics Engineers), USA.

D. Graupe, "Principles of Artificial Neural Networks," Advanced Series on Circuits and Systems—vol. 3—Book, 1999, 1 (7 pp.), World Scientific Publishing Co. Pte. Ltd., Singapore.

A. Cichocki et al., "Blind Separation and Filtering Using State Space Models," Circuits and Systems, 1999, ISCAS '99, Proceedings of the 1999 IEEE International Symposium on Orlando, FL, USA, IEEE, US, vol. 5, May 30, 1999, pp. V78-V81, XP002287269, ISBN: 0-7803-5471-0, the whole document.

* cited by examiner

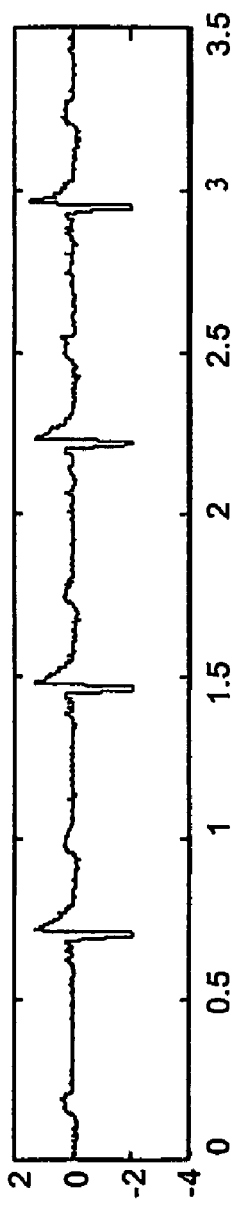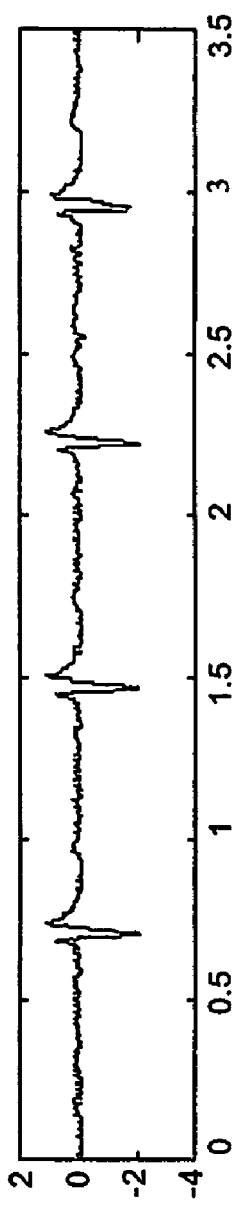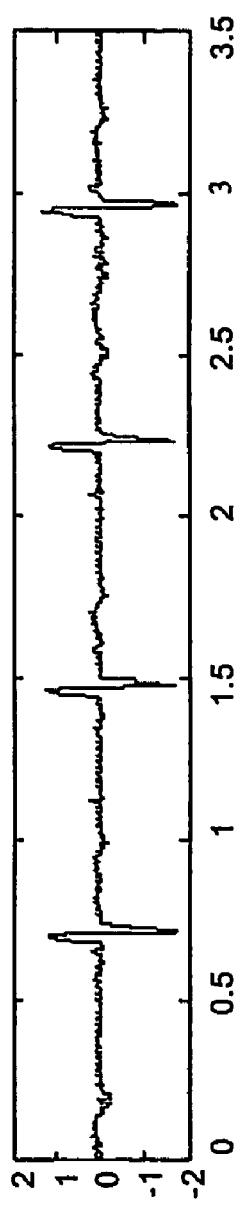

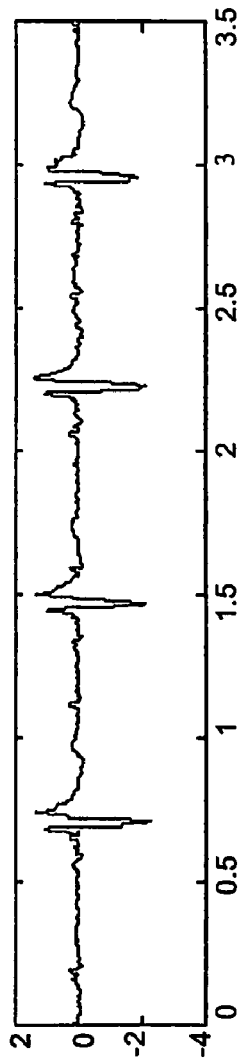
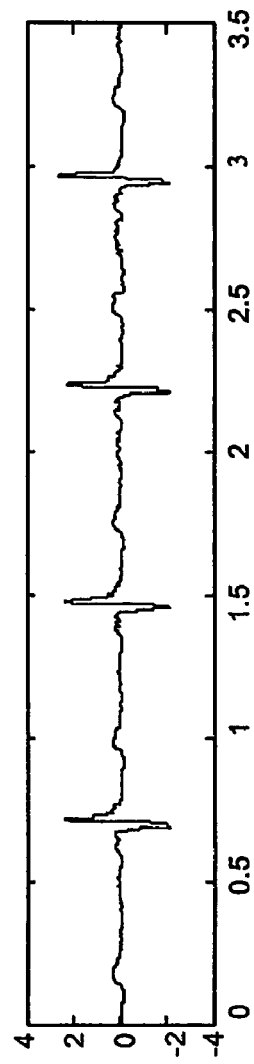
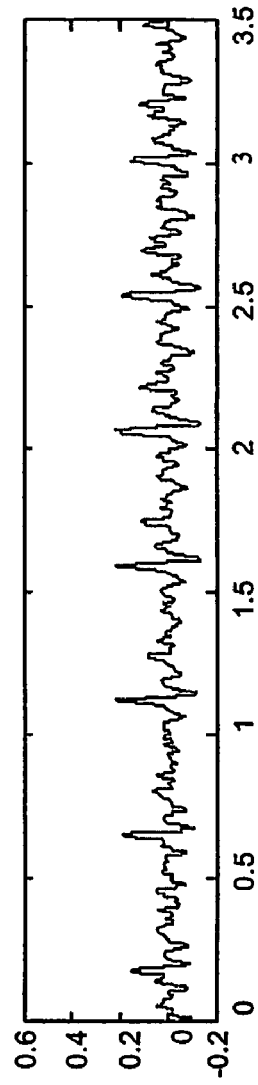
FIG. 9
FIG. 10
FIG. 11

SEPARATION OF ONE OR MORE FETAL HEART COMPONENT SIGNALS FROM HEART SIGNAL INFORMATION OBTAINED FROM A PREGNANT FEMALE

CROSS-REFERENCE TO RELATED APPLICATION

This application claims the priority of U.S. provisional Patent Application Ser. No. 60/516,343 (by Graupe, et al., filed Oct. 31, 2003, and entitled "SEPARATION OF ONE OR MORE FETAL HEART COMPONENT SIGNALS FROM HEART SIGNAL INFORMATION OBTAINED FROM A PREGNANT FEMALE").

TECHNICAL FIELD

The invention relates generally to the medical arts and more particularly to heart signal information.

BACKGROUND

Doctors today employ one or more heart signal machines to make a determination of one or more fetal heart component signals. The heart signal machine obtains heart signal information from a pregnant mother. The heart signal machine in one example comprises one or more processor components. The heart signal machine employs the processor components to make a determination of the fetal heart component signal based on the heart signal information.

In one example, the heart signal machine comprises an ultrasound machine. The ultrasound machine in one example allows the doctor to view heart muscle movement of the fetus. For example, the doctor infers the fetal heart component signal from the heart muscle movement. One shortcoming of an employment of the ultrasound machine to infer the fetal heart component signal is that the heart component signal is not a measurement of the electrical activity of fetal heart muscle movement. For example, the doctor could only diagnose major defects of the fetal heart through employment of the ultrasound machine.

In another example, the heart signal machine comprises a magnetocardiogram ("MCA") machine and the heart signal information comprises magnetic heart signal information. The magnetocardiogram machine in one example employs one or more magnets to obtain the magnetic heart signal information from the pregnant mother. The processor component of the magnetocardiogram machine employs the magnetic heart signal information to make a determination of the fetal heart component signal. One shortcoming of an employment of the magnetocardiogram machine to make the determination of the fetal heart component signal is that the magnetocardiogram machine is expensive.

In yet another example, the heart signal machine comprises an electrocardiogram ("ECG") machine and the heart signal information comprise electrical heart signal information. The electrocardiogram machine in one example employs one or more electrodes to obtain the electrical heart signal information from the pregnant mother. Diagnostic information can best be obtained from a fetal electrocardiogram. However access to that fetal electrocardiogram in a noninvasive manner is not available early in the pregnancy. The fetus' electrocardiogram is extremely weak early in the pregnancy. Not only is the fetus' electrocardiogram extremely weak in relation to the maternal electrocardiogram in which it is embedded, but it is also weak in relation to the various noises picked up by the electrocardiogram electrodes. The noises are partly due to electromyographic ("EMG") activity picked up by these electrodes, especially when the electrodes are placed on the mother's abdomen or lower back.

The processor component of the electrocardiogram machine in one example employs independent component analysis ("ICA") to separate the fetal electrical heart component signal from the electrical heart signal information. One shortcoming of an employment of the electrocardiogram machine to determine the fetal electrical heart component signal is that the fetal electrical heart component signal can have an amplitude that is $\frac{1}{2,000}$ of the amplitude of a maternal electrical heart component signal in the $12^{th}$ to $15^{th}$ week of pregnancy. Furthermore, the electrocardiogram machine cannot separate very weak fetal heart signals, such as fetal heart signals early in the pregnancy at the $12^{th}$ to $25^{th}$ gestation week. The fetal electrical heart component signal in one example is embedded in noise that has a greater amplitude than the fetal electrical heart component signal. Thus, the noise makes it difficult to accurately determine the fetal electrical heart component signal in a noninvasive manner. The electrocardiogram machine alone cannot separate a major portion of the noise component signal from the fetal electrical heart component signal. Thus, the doctor is unable to diagnose one or more fetal heart defects early enough into the pregnancy to treat the fetal heart defects.

The fetal electrocardiogram separation problem is complicated by the fact that the noise in each electrocardiogram recording channel is different from that in the other channels. Classic singular value decomposition type (including independent component analysis based) separation methods must assume that the number of incoming signals (channels) is smaller or equal to the number of uncorrelated or independent sources that form the incoming sources. However, this is not the case in the fetal electrocardiogram separation problem due to the different statistics of the noises in the various channels. Hence, if there were one noise common to all electrodes in a three channel situation, then the number of source signals considered in the fetal electrocardiogram separation problem would have been three, namely, fetal electrocardiogram, maternal electrocardiogram, and noise. However, in reality there are five sources in the three channel fetal electrocardiogram separation problem. The five sources are the fetal electrocardiogram, the maternal electrocardiogram, and three noises of different statistics. For example, each channel has a separate noise signal. This mixture cannot be separated by classical separation algorithms of any type unless all three noises are of considerably lower signal-power than the fetal electrocardiogram signal power. However, early in a pregnancy, the three noises are not of considerably lower signal-power than the fetal electrocardiogram signal power.

Thus, a need exists for a heart signal machine that can separate a fetal heart component signal from heart signal information obtained from a pregnant female.

SUMMARY

The invention in one implementation encompasses a method. One or more fetal heart component signals are separated from heart signal information obtained from a pregnant female based on singular value decomposition.

Another implementation of the invention encompasses an apparatus. The apparatus comprises one or more processor components that separate one or more fetal heart component signals from heart signal information obtained from a pregnant female based on singular value decomposition.

Yet another implementation of the invention encompasses an article. The article comprises: one or more computer-readable signal-bearing media; and means in the one or more media for separating one or more fetal heart component signals from heart signal information obtained from a pregnant female based on singular value decomposition.

Still yet another implementation of the invention encompasses a method. One or more filters are employed to extract one or more fetal heart component signals from heart signal information obtained from a pregnant female. The one or more fetal heart component signals are separated from the heart signal information based on independent component analysis. One or more blind adaptive filtering components are employed to reduce noise in the one or more fetal heart component signals.

A further implementation of the invention encompasses an apparatus. The apparatus comprises one or more processor components that cause one or more filters to extract one or more fetal heart component signals from heart signal information obtained from a pregnant female. A first one or more of the one or more processor components separate the one or more fetal heart component signals from the heart signal information based on independent component analysis. A second one or more of the one or more processor components employ one or more blind adaptive filtering components to reduce noise in the one or more fetal heart component signals.

Another implementation of the invention encompasses an article. The article comprises: one or more computer-readable signal-bearing media; means in the one or more media for employing one or more filters to extract one or more fetal heart component signals from heart signal information obtained from a pregnant female; means in the one or more media for separating the one or more fetal heart component signals from the heart signal information based on independent component analysis; and means in the one or more media for employing a cepstral analysis to reduce noise in the one or more fetal heart component signals.

DESCRIPTION OF THE DRAWINGS

Features of exemplary implementations of the invention will become apparent from the description, the claims, and the accompanying drawings in which:

FIG. 6 is a representation of an exemplary plot of heart signal information obtained through a first channel of the heart signal machine of the apparatus of FIG. 1.

FIG. 7 is a representation of an exemplary plot of heart signal information obtained through a second channel of the heart signal machine of the apparatus of FIG. 1.

FIG. 8 is a representation of an exemplary plot of heart signal information obtained through a third channel of the heart signal machine of the apparatus of FIG. 1.

FIG. 9 is a representation of one exemplary plot of a maternal heart component signal obtained through employment of the heart signal machine of the apparatus of FIG. 1.

FIG. 10 is a representation of another exemplary plot of a maternal heart component signal obtained through employment of the heart signal machine of the apparatus of FIG. 1.

FIG. 11 is a representation of an exemplary plot of a fetal heart component signal obtained through employment of the heart signal machine of the apparatus of FIG. 1.

DETAILED DESCRIPTION

Referring to the BACKGROUND section above, to overcome the difficulties of fetal ECG separation, a singular value decomposition based separation sub-system is combined with a noise-reduction sub-system for an approach based on blind adaptive filtering. Exemplary techniques for performing blind adaptive filtering are disclosed in D. Graupe and D. Veselinovic, Blind Adaptive Filtering of Speech from Unknown Noise of Unknown Spectrum Using a Virtual Feedback Configuration, IEEE Transactions on Speech and Audio Processing, Vol. 8, No. 2, March 2000, pp. 146-158; or in D. Veselinovic and D. Graupe, A Wavelet Transform Approach to Blind Adaptive Filtering of Speech from Unknown Noises, IEEE Transactions on Circuits & Systems—Part II, Vol. 50, No. 3, March 2003, pp. 150-154; or in Chapters 11 and 12 of D. Graupe, Time Series Analysis, Identification and Adaptive Filtering, Kreiger Publishing Co., Melbourne, Fla., 1984, second revised edition, 1989; or by cepstral filtering methods that employ a Fourier transform of a nonlinear function of another Fourier transform; or in A. Oppenheim and R. Schafer, Digital Signal Processing, Prentice-Hall, Inc., Englewood Cliffs, N.J., 1975, pp 500-507.

In one example, one or more fetal heart component signals are separated from heart signal information obtained from a pregnant female based on singular value decomposition. A further example incorporates filtering components, based on nonlinear blind adaptive filtering methods, to reduce the effects of measurement noises that otherwise preclude adequate retrieval of the fetal heart information early in the pregnancy when measurement noises are high in relation to the fetal heart signal.

Figure 1:
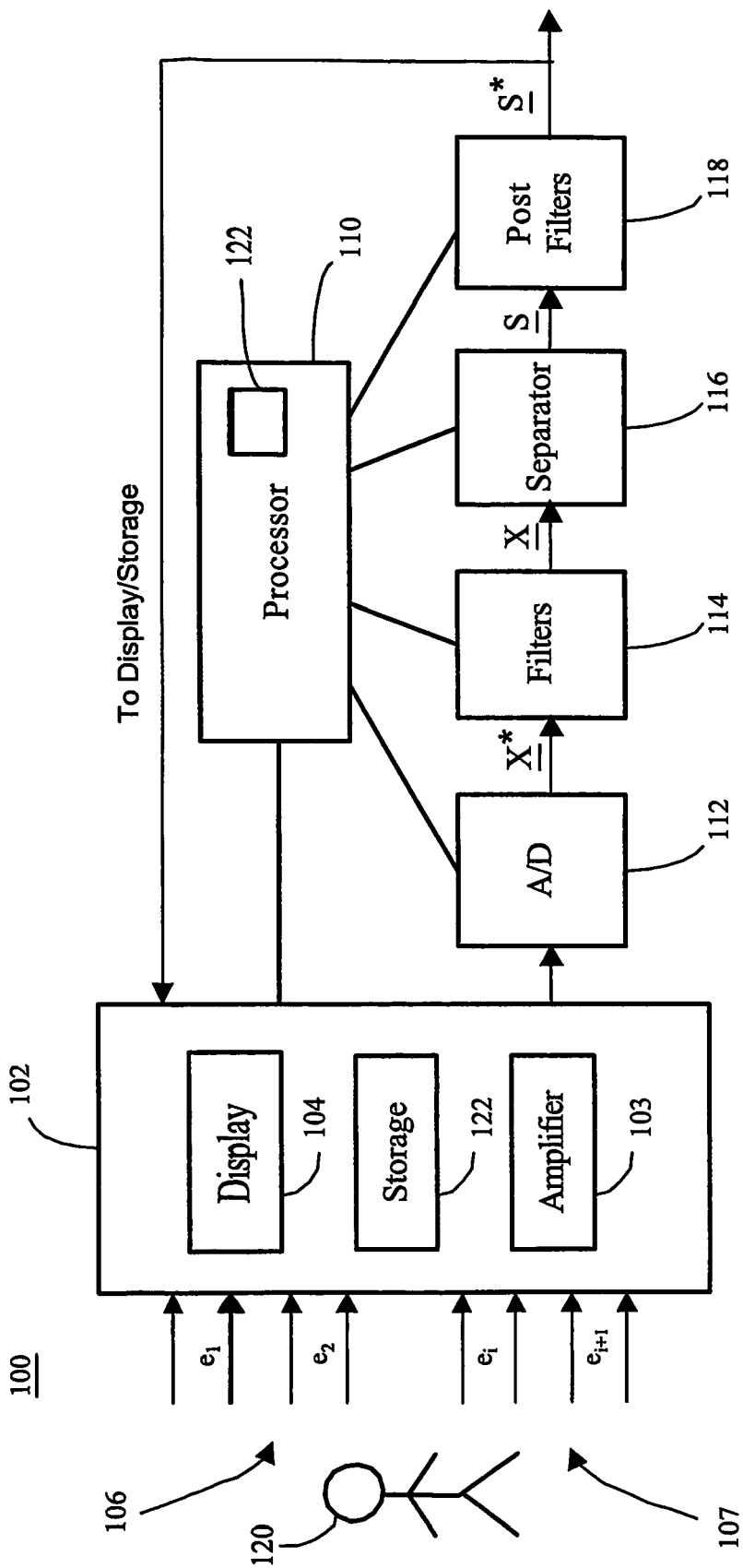
FIG. 1 is a representation of one exemplary implementation of an apparatus that comprises a heart signal machine, a plurality of electrode pairs, one or more processor components, one or more analog-to-digital converters, one or more filters, one or more separator components, and one or more post filters, wherein the plurality of electrode pairs comprise a plurality of an abdominal electrode pair and a chest electrode pair.
Figure 2:
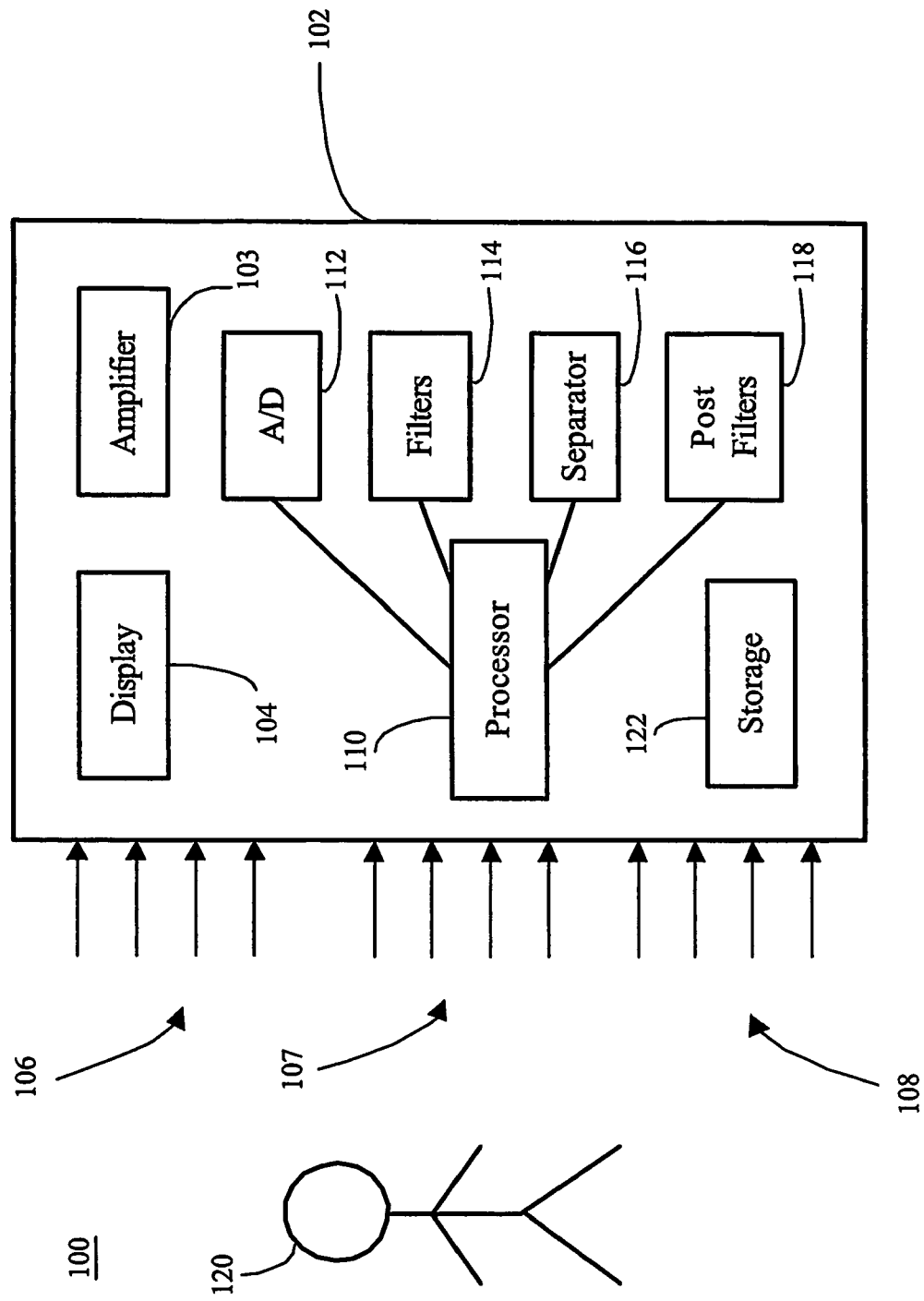
FIG. 2 is a representation of another exemplary implementation of the apparatus of FIG. 1, wherein the plurality of electrode pairs comprise an abdominal electrode pair, a chest electrode pair, and a thoracic electrode pair.

Turning to FIGS. 1-2, an apparatus 100 in one example comprises a plurality of components such as computer software and/or hardware components. A number of such components can be combined or divided in the apparatus 100. An exemplary component of the apparatus 100 employs and/or comprises a set and/or series of computer instructions written in or implemented with any of a number of programming languages, as will be appreciated by those skilled in the art.

The apparatus 100 in one example comprises a heart signal machine 102, one or more electrode pairs 106, 107, and 108, one or more processor components 110, one or more analog-to-digital converters 112, one or more filters 114, one or more separator components 116, and one or more post filters 118. A vector channel runs between the analog-to-digital converter 112 and the filters 114, between the filters 114 and the separator component 116, and between the separator component 116 and the post filters 118.

The heart signal machine 102 obtains heart signal information from a pregnant woman 120. The processor component 110 in one example, as in FIG. 2, employs one or more electrode pairs 106, 107, and 108 (e.g., $e_1$, $e_2$, $e_i$, and $e_{i+1}$) to record the heart signal information from the pregnant woman 120. The processor component 110 in one example employs one or more of the analog-to-digital converter 112, the filter 114, the separator component 116, and the post filter 118 to separate one or more fetal heart component signals from the heart signal information. For example, the processor component 110 can separate the fetal heart component signals that have an amplitude as low as $\frac{1}{2,000}$ of the amplitude of the non-fetal heart component signals and as early as 12 weeks into the pregnancy of the pregnant mother 120.

Referring to FIGS. 1 and 6-11, the heart signal machine 102 in one example employs one or more of the electrode pairs 106, 107, and 108 and the processor component 110 to output to a doctor the heart signal information of one or more fetuses of the pregnant woman 120. The electrode pairs 106, 107, and 108 capture raw heart signal data, such as the raw heart signal data 602, 702 and 802 of FIGS. 6-8. The raw heart signal data 602, 702, and 802 in one example comprise mixtures of a fetal heart component signal, a maternal heart component signal, and a mixture of several noise component signals from the various electrode pairs 106, 107, and 108. The heart signal machine 102 receives the raw heart signal data 602, 702 and 802 and in one example separates the mixed signal components to output a first maternal heart signal 902, a second maternal heart signal 1002, and a fetal heart signal 1102, as shown in FIGS. 9-11.

Figure 12:
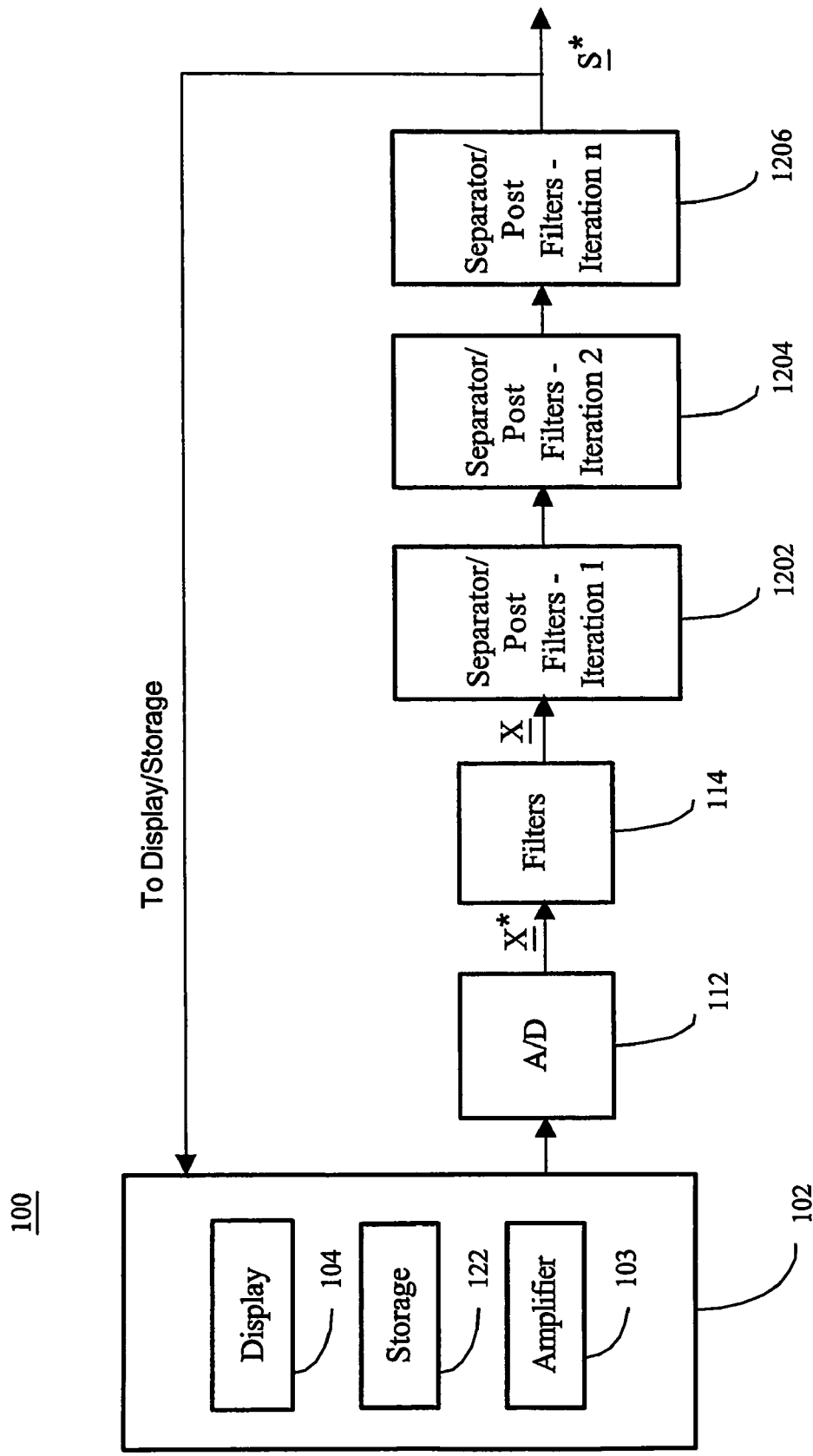
FIG. 12 is a representation of an iterative version of the apparatus of FIG. 1.

Referring to FIGS. 1 and 12, the heart signal machine 102 comprises an instance of a recordable data storage medium 122. In one example, the heart signal machine 102 comprises an electrocardiogram ("ECG") machine. For example, where the heart signal information comprises a plurality of electrocardiogram signals, the heart signal machine 102 outputs one or more electrocardiogram signals. In another example, the heart signal machine 102 comprises a magnetocardiogram ("MCG") machine. For example, where the heart signal information comprises a plurality of magnetocardiogram signals, the heart signal machine 102 outputs one or more magnetocardiogram signals. FIG. 1 illustrates a first separation approach and FIG. 12 illustrates a realization of the apparatus 100 where components are cascaded one or more times to perform an iterative separation.

In FIG. 12, the functionality of the separator component 116 and the post filter 118 are combined into a series of iterative separators 1202, 1204, and 1206. A set of estimated separation signals is passed through the series of iterative separators 1202, 1204, and 1206. Each estimated separation signal of one separation iteration is cross-correlated with each other estimated separation signal of the one separation iteration after each separation iteration. An absolute value of the cross-correlations is evaluated at each iteration and the outcome of the multi-step iterative separator is output once a maximal absolute value of the cross correlations is below a pre-determined threshold value. Alternatively, the outcome of the multi-step iterative separator may be output once a sum of absolute values of the cross correlations is below a pre-determined threshold value.

Referring to FIGS. 1 and 2, the heart signal machine 102 comprises one or more of an amplifier component 103, a display component 104, the processor component 110, the analog-to-digital converter 112, the filter 114, the separator component 116, and the post filter 118. In one example, the processor component 110, the analog-to-digital converter 112, the filter 114, the separator component 116, and the post filter 118 connect to the heart signal machine 102 through one or more signal cables, as shown in FIG. 1. In another example, the processor component 110, the analog-to-digital converter 112, the filter 114, the separator component 116, and the post filter 118 are integrated into the heart signal machine 102, as shown in FIG. 2. For example, the processor component 110 in FIG. 2 is an integral part of the heart signal machine 102.

Referring to FIGS. 1 and 6-11, after separation of the first maternal heart signal 902, the second maternal heart signal 1002, and the fetal heart signal 1102 from the raw heart signal data 602, 702 and 802, the display component 104 may output one or more of the fetal heart component signal 1102, and/or the first and second maternal heart component signals 902 and 1002. The processor component 110 in one example sends the fetal heart component signal 1102 from the output of the post filter 118 to the display component 104 to display the fetal heart component signal to the doctor. The doctor employs the display component 104 of the heart signal machine 102 to choose to view the fetal heart component signal, the maternal heart component signal, or the noise component signals.

Referring to FIGS. 1-2, the electrode pairs 106, 107, 108 connect with the heart signal machine 102 and/or the processor component 110. The processor component 110 in one example employs the electrode pairs 106, 107, 108 to obtain the heart signal information from the pregnant mother 120. The electrode pairs 106, 107, 108 comprise a ground component signal and measurement component signal. The electrode pair 106 in one example comprises a chest electrode pair. The electrode pair 107 in one example comprises an abdominal electrode pair. The electrode pair 108 in one example comprises a thoracic electrode pair. The processor component 110 employs at least three total electrode pairs of the electrode pairs 106, 107, and 108 to obtain the heart signal information. In one example, the processor component 110 obtains the heart signal information from one or more of the electrode pairs 106 and two or more of the electrode pairs 107. For example in FIG. 1, the processor component 110 does not obtain the heart signal information from the electrode pair 108. In another example, the processor component 110 employs eight to ten total electrode pairs of the electrode pairs 106, 107, and 108 to obtain the heart signal information.

The processor component 110 in one example employs one or more of the analog-to-digital converter 112, the filters 114, the separator component 116, and the post filter 118 to separate the fetal heart component signal from the heart signal information. The processor component 110 in one example passes the heart signal information from the electrodes 106, 107, and 108 to the analog-to-digital converter 112.

The analog-to-digital converter 112 in one example receives the heart signal information from the processor component 110. For example, the processor component 110 employs the analog-to-digital converter 112 to digitize the heart signal information. The analog-to-digital converter 112 in one example outputs a vector of the plurality of signals [X*] based on the heart signal information to the processor component 110 or the filters 114.

Figure 3:
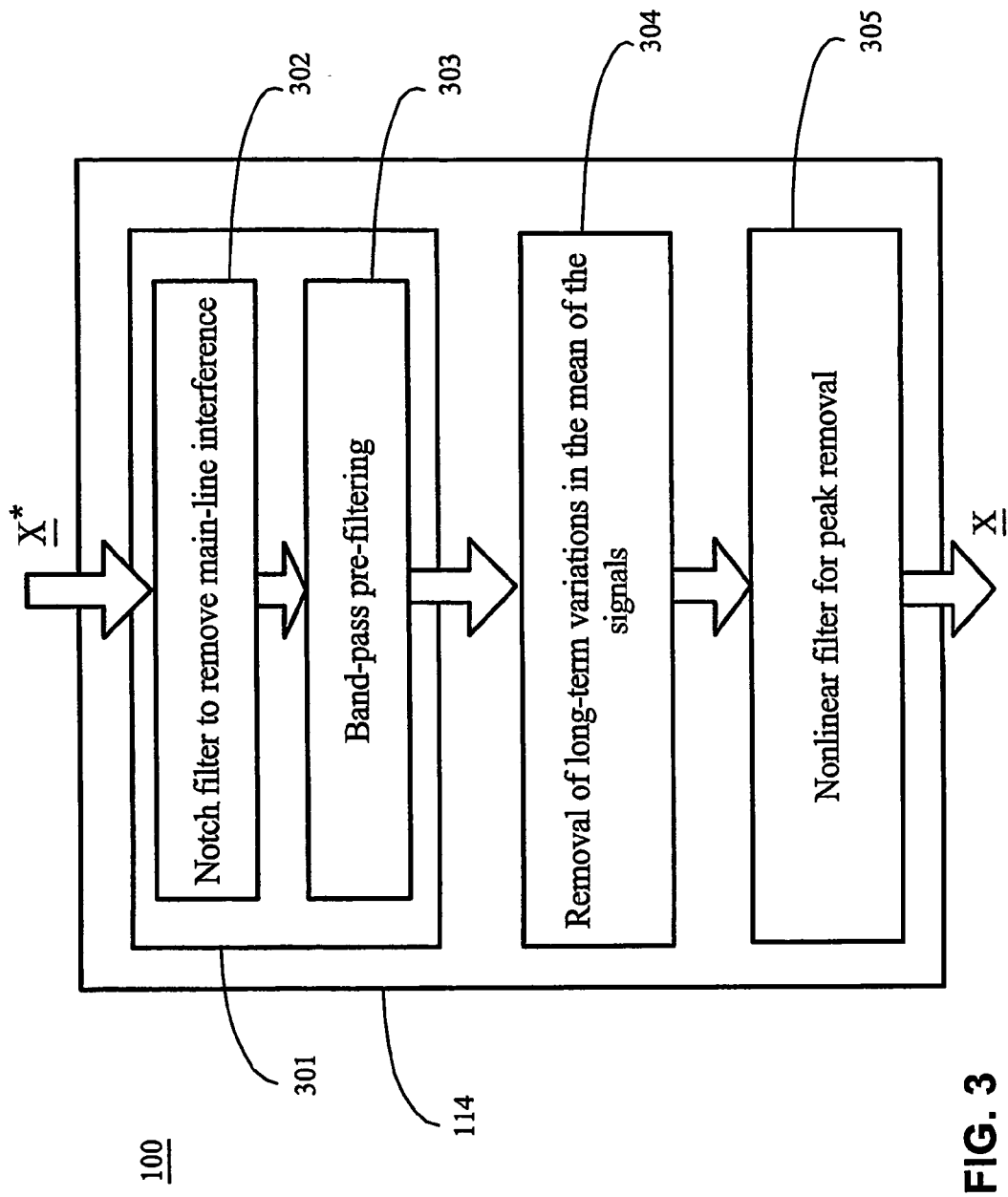
FIG. 3 is one exemplary implementation of the filter of the apparatus of FIG. 1.

Referring to FIGS. 1 and 3, the filters 114 in one example receive the heart signal information or the vector of the plurality of signals from the processor component 110 or the analog-to-digital converter 112. The processor component 110 in one example employs the filters 114 to re-process the heart signal information prior to its separation in separator component 116 of FIG. 1. In one example, the filter component 114 comprises of a cascade of linear and nonlinear filters, as shown in FIG. 3. Filter 301 comprises a linear filter that serves in one example to remove power-main-line interference from the heart signal information. For example, the filter 301 comprises one or more notch (band-stop) filters 302 followed by low-pass linear filter 303 for frequencies that lie above the frequency spectrum of electrocardiogram signals, including any fetal electrocardiogram signals. The output of filter 301 is input into filter 304 which removes long-term variations (non-stationarities) in the mean of each of the long-term signals. The filter 304 in one example comprises a high pass filter with a cut-off frequency that is one-third or less of the average frequency of a maternal heart rate to remove effects of time-variations in a long term mean of the heart signal information between maternal heart beats. The filter 304 may employ one or more stages of differencing to remove effects of time-variations in the long term mean of the heart signal information between maternal heart beats.

In one example, the output of filter 304 is input into non-linear filter 305 to reduce excessive high amplitude peaks from the incoming heart signals. First, the filter 305 raises the heart signal to a power greater than one (i.e., p>1). Second, the filter 305 reduces the peaks of the power-raised signal that exceeded the predetermined threshold value. Third, the filter 305 raises the signal of reduced peaks to an inverse of the power (i.e., 1/p). The filter 305 preserves the signs of the signals received at the input of filter 305.

Figure 4:
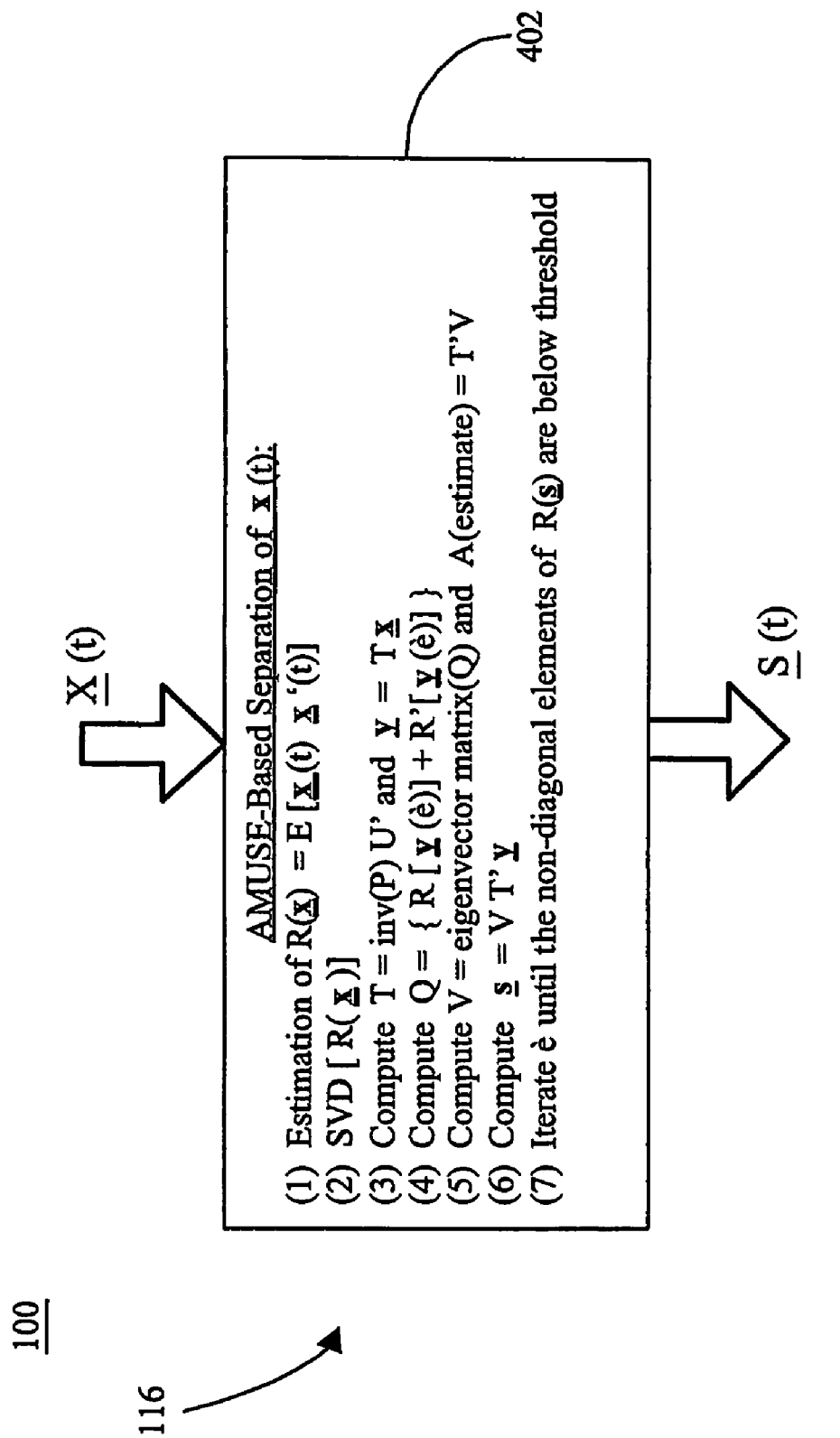
FIG. 4 is one exemplary implementation of the separator component of the apparatus of FIG. 1.

Referring to FIGS. 1 and 4, upon receipt of the output from the filters 114, the processor component 110 in one example employs the one or more separator components 116 to perform a separation 402 of the second portion of the vector of the plurality of signals into [S]: the fetal heart component signal, the maternal heart component signal, and the noise component signals. For example, the separation 402 is based on singular value decomposition ("SVD"), as shown in FIG. 4. In one example, the separator component 116 in one example employs an AMUSE-based algorithm to perform singular value decomposition for the blind separation 402.

In one example, base techniques for performing the AMUSE-based algorithm are disclosed in Tong, L., Liu, R. W., Soon, V. C. and Huang, Y., 1991, Indeterminacy and Identifiability of Blind Identification, IEEE Transactions On Circuits and Systems, Vol. 38, No. 5, May 1991, pp. 499-509. In another example, techniques for performing the AMUSE-based algorithm are based on a variation where the delay parameter involved in the AMUSE-based algorithm is computed to minimize cross-correlations between output components, while avoiding removal of low eigenvalues in contrast to the pervious version of the separator. An exemplary technique for performing the variation is disclosed in Suliga, P. and Graupe, D., A Neural Network Approach to Blind Separation of Mixed Signals, Smart Engineering Systems Design, Vol. 12, ASME Press, NY, 2002, pp. 689-694.

In another example, the separator component 116 employs a neural network algorithm to perform singular value decomposition for the separation 402. An exemplary technique for performing the neural network algorithm is disclosed in Suliga, P. and Graupe, D., A Neural Network Approach to Blind Separation of Mixed Signals, Smart Engineering Systems Design, Vol. 12, ASME Press, NY, 2002, pp. 689-694. The separator component 116 in one example employs a singular value decomposition related approach using independent component analysis to make a determination of a blind separator for blind separation analysis. For example, the separator component 116 performs blind separation analysis to separate the second portion of the vector of the plurality of signals into the fetal heart component signal, the maternal heart component signal, and the noise component signals. The noise component signals in one example are not correlated with the fetal heart component signal or with the maternal heart component signal. The separator component 116 passes the fetal heart component signal, the maternal heart component signal, and the noise component signals to one or more of the processor component 110 and the post filter 118.

Figure 5:
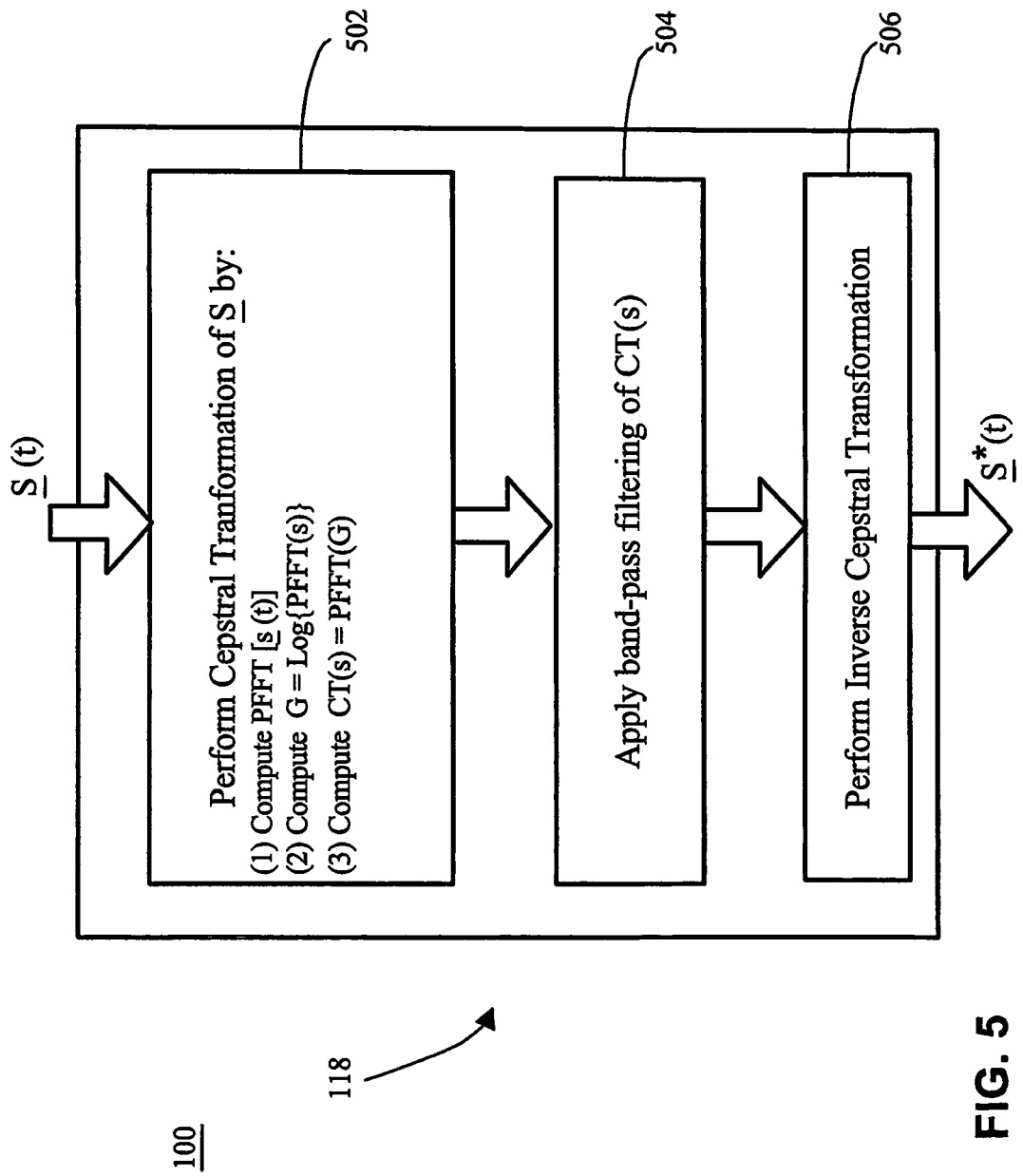
FIG. 5 is one exemplary implementation of the post filter of the apparatus of FIG. 1.

Referring to FIGS. 1 and 5, upon receipt of the outputs from the separator component 116, the processor component 110 employs the post filter 118 to reduce one or more of the remnant noise components and the maternal heart signal components from the fetal heart component signal. The remnant noise components in one example comprise colored and/or white noise components.

The post filter 118 in one example employs a cepstral component 502 to reduce the remnant noise components from the fetal heart component signal, the maternal heart component signal, and the noise component signal as received from the output of the separator component 116, thus serving as a cepstral-based blind adaptive filter. The cepstral component 502 in one example performs a first cepstral transform function on the fetal heart component signal, the maternal heart component signal, and the noise component signals.

In one example, the cepstral component 502 estimates which of the outputs from the separator component 116 is most closely correlated with the signal from the maternal chest electrode pair. Then, the cepstral component 502 reduces the effect of the cepstral transformation of the estimated maternal signal on the cepstral transformations of the other signals coming from the separator component 116. For example, the cepstral component 502 passes its outputs through a cepstral filter 504. Subsequently, the post filter 118 performs an inverse cepstral transformation 506 on the output of the cepstral filter 504. In another example, the cepstral component 502 performs a cepstral transformation on the signal from the maternal chest electrode pair at the output of the filters 114 and employs this transformation as being the closest to the actual maternal signal component in its filtering operation. In yet another example, the cepstral-based post-filtering component 502 considers prior knowledge on cepstral analysis of electrocardiogram signals relating to fetal electrocardiograms.

In another example, the post filter 118 may perform wavelet filtering of the signals from the separator component 116. Subsequently, the post filter 118 reduces the effect of the wavelet transform of the signal component that is closest to the maternal heart signal. For example, the post-filtering component 502 compares the cross-correlations with the maternal chest signal on the wavelet transform of the other signals coming from the filters 114. The post-filtering component 502 reduces the effect of this wavelet transform in the wavelet transformations of the other signals input to the post-filtering component 502 and then inverse wavelet transforms the resultant wavelet transformations, such that it serves as a blind adaptive filter. In another example of using a wavelet transform filter in the post-filtering component 502, the wavelet transform of the heart signal component that relates to the maternal chest electrode pair, as output from filters 114 is employed as that of the wavelet transform of the maternal heart signal.

In yet another example, the post filter 118 uses frequency domain blind adaptive filtering ("BAF") to reduce the effects of maternal heart signals and of noise on the fetal heart signal. An exemplary technique for performing frequency domain blind adaptive filtering is disclosed in D. Graupe and D. Veselinovic, Blind Adaptive Filtering of Speech from Unknown Noise of Unknown. Spectrum Using a Virtual Feedback Configuration, IEEE Transactions on Speech and Audio Processing, Vol. 8, No. 2, March 2000, pp. 146-158. In one example, as part of its blind adaptive filtering algorithm, the blind adaptive filter employs identified parameters, but when employing parameters identified from the maternal heart signal related to the output of the filter component 114 and parameters are available from prior information on echocardiogram signals in general, the prior parameters are employed by the blind adaptive filter.

Other examples of the post filter 118 comprise a Wiener and Kalman filters. The Wiener and Kalman filters may serve as the filtering algorithm in the blind adaptive filter. Exemplary techniques for performing Wiener and Kalman filters are disclosed in Chapters 11 and 12 of D. Graupe, Time Series Analysis, Identification and Adaptive Filtering, Kreiger Publishing Co., Melbourne, Fla., 1984, second revised edition, 1989

Upon receipt of the reduced-noise fetal heart component signal, the reduced-noise maternal heart component signal, and the noise component signals, the processor component 110 passes the reduced-noise fetal heart component signal, the reduced-noise maternal heart component signal, and the noise component signals to the display component 104 of the heart signal machine 102. The doctor in one example is able to view on the display component 104 the fetal heart component signal to make a determination of the health of the heart of the fetus. For example, the doctor can employ the determination of the health to diagnose and/or treat one or more heart defects of the fetus as early as the 12th week into the pregnancy of the pregnant woman 120 through employment of the heart signal machine 102.

The apparatus 100 in one example employs one or more computer-readable signal-bearing medium. Examples of a computer-readable signal-bearing medium for the apparatus 100 comprise the recordable data storage medium 122 of the heart signal machine 102 and the processor component 110. For example, the recordable data storage medium for the apparatus 100 comprises one or more of a magnetic, electrical, optical, biological, and atomic data storage medium. In one example, the computer-readable signal-bearing medium comprises a modulated carrier signal transmitted over a network comprising or coupled with the apparatus 100, for instance, one or more of a telephone network, a local area network ("LAN"), the internet, and a wireless network.

The steps or operations described herein are just exemplary. There may be many variations to these steps or operations without departing from the spirit of the invention. For instance, the steps may be performed in a differing order, or steps may be added, deleted, or modified.

Although exemplary implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. A method, comprising the step of:
    separating one or more fetal heart component signals from heart signal information obtained from a pregnant female based on singular value decomposition, wherein the step of separating the one or more fetal heart component signals from the heart signal information obtained from the pregnant female based on singular value decomposition comprises the steps of:
    computing a singular value decomposition of a covariance matrix of the heart signal information to yield a set of output signals;
    computing a delay parameter to minimize an absolute value of cross-correlations between the set of output signals;
    taking a singular value decomposition of the sum of a covariance matrix of the set of output signals; and
    taking a singular value decomposition of a transpose of the covariance matrix of the set of output signals to yield a separated output estimate of the one or more fetal heart component signals.

2. The method of claim 1, wherein the step of separating the one or more fetal heart component signals from the heart signal information obtained from the pregnant female based on singular value decomposition comprises the step of:
    employing one or more analog-to-digital converters to digitize the heart signal information upon receipt of the heart signal information.

3. The method of claim 1, wherein the step of separating the one or more fetal heart component signals from the heart signal information obtained from the pregnant female based on singular value decomposition comprises the step of:
    employing one or more filtering components to reduce one or more amplitudes of one or more components of the heart signal information.

4. The method of claim 3, wherein the step of employing the one or more filtering components to reduce the one or more amplitudes of the one or more components of the heart signal information comprises the step of:
    employing one or more non-linear filters and one or more non-linear inverse filters to reduce the one or more amplitudes of the one or more components of the heart signal information.

5. The method of claim 1, wherein the heart signal information comprises the one or more fetal heart component signals, one or more maternal heart component signals, and one or more noise component signals, wherein the step of separating the one or more fetal heart component signals from the heart signal information obtained from the pregnant female based on singular value decomposition comprises the steps of:
    determining one or more blind separators based on singular value decomposition; and
    employing the one or more blind separators to separate the one or more fetal heart component signals from the one or more maternal heart component signals and the one or more noise component signals.

6. The method of claim 1, wherein the step of separating the one or more fetal heart component signals from the heart signal information obtained from the pregnant female based on singular value decomposition comprises the steps of:
    employing one or more cepstral transformation components to identify one or more noise components in the one or more fetal heart component signals;
    reducing one or more amplitudes of the one or more noise components in the one or more fetal heart component signals to change the one or more fetal heart component signals into one or more reduced noise fetal heart component signals; and
    employing one or more inverse cepstral transformation components to output one or more of the one or more reduced noise fetal heart component signals.

7. The method of claim 1, wherein the heart signal information comprises the one or more fetal heart component signals, one or more maternal heart component signals, and one or more noise component signals, wherein the step of separating the one or more fetal heart component signals from the heart signal information obtained from the pregnant female based on singular value decomposition comprises the steps of:
    employing one or more analog-to-digital converters to digitize the heart signal information upon receipt of the heart signal information;
    employing one or more non-linear filters and one or more non-linear inverse filters to reduce one or more amplitudes of one or more components of the heart signal information;
    determining one or more blind separators based on singular value decomposition; and
    employing the one or more blind separators to separate the one or more fetal heart component signals from the one or more maternal heart component signals and the one or more noise component signals.

8. The method of claim 7, further comprising the steps of:
    employing one or more cepstral transformation components to identify one or more noise components in the one or more fetal heart component signals;
    reducing one or more amplitudes of the one or more noise components in the one or more fetal heart component signals to change the one or more fetal heart component signals into one or more reduced noise fetal heart component signals; and
    employing one or more inverse cepstral transformation components to output one or more of the one or more reduced noise fetal heart component signals.

9. The method of claim 7, further comprising the step of:
employing a high pass filter with a cut-off frequency that is one-third or less of the average frequency of a maternal heart rate to remove effects of time-variations in a long term mean of the heart signal information between maternal heart beats.

10. The method of claim 7, further comprising the step of:
employing one or more stages of differencing between successive samples of the heart signal information to remove effects of time-variations in a long term mean of the heart signal information between maternal heart beats.

11. The method of claim 7, wherein the one or more blind separators comprise a multi-step iterative separator, wherein the step of employing the one or more blind separators to separate the one or more fetal heart component signals from the one or more maternal heart component signals and the one or more noise component signals comprises the steps of:
passing a set of estimated separation signals from a first separation iteration to a next separation iteration;
creating cross-correlations of each estimated separation signal of one separation iteration with each other estimated separation signal of the one separation iteration after each separation iteration;
evaluating an absolute value of the cross-correlations; and
outputting the outcome of the multi-step iterative separator once a maximal absolute value of the cross correlations is below a pre-determined threshold value.

12. The method of claim 11, wherein the step of outputting the outcome of the multi-step iterative separator once the maximal absolute value of the cross correlations is below the pre-determined threshold value comprises the step of:
entering the set of estimated separation signals as initialization parameters to an artificial neural network that iteratively outputs incremental changes to the initialization parameters until the maximal absolute value is below the pre-determined threshold value.

13. The method of claim 7, wherein the one or more blind separators comprise a multi-step iterative separator, wherein the step of employing the one or more blind separators to separate the one or more fetal heart component signals from the one or more maternal heart component signals and the one or more noise component signals comprises the steps of:
passing a set of estimated separation signals from a first separation iteration to a next separation iteration;
creating cross-correlations of each estimated separation signal of one separation iteration with each other estimated separation signal of the one separation iteration after each separation iteration;
evaluating an absolute value of the cross-correlations; and
outputting the outcome of the multi-step iterative separator once a sum of absolute values of the cross correlations is below a pre-determined threshold value.

14. The method of claim 13, wherein the step of outputting the outcome of the multi-step iterative separator once the sum of the absolute values of the cross correlations is below the pre-determined threshold value comprises the step of:
entering the set of estimated separation signals as initialization parameters to an artificial neural network that iteratively outputs incremental changes to the initialization parameters until the sum of the absolute values is below the pre-determined threshold value.

15. The method of claim 1, wherein the heart signal information comprises multi channel information of mixtures in different mixing combinations of at least three different types of signals, one being maternal electrocardiogram, one being fetal electrocardiogram, and one being noise;
wherein the step of separating the one or more fetal heart component signals from the heart signal information obtained from the pregnant female based on singular value decomposition comprises the steps of:
employing at least three channels to obtain the heart signal information;
placing a first pair of electrodes on a chest of the pregnant female; and
placing a second pair of electrodes on an abdomen or lower back of the pregnant female to obtain a portion of the heart signal information closer to a heart of the fetus.

16. The method of claim 1, further comprising the step of:
passing the separated output estimate through a blind adaptive filter to identify parameters of the separated output estimate, wherein the blind adaptive filter uses the parameters to adapt a filtering algorithm to reduce noise of the separated output estimate.

17. The method of claim 16, further comprising the step of:
reentering outputs of the blind adaptive filter into a singular value decomposition to undergo another round of separation.

18. The method of claim 16, wherein the heart signal information comprises the one or more fetal heart component signals, one or more maternal heart component signals, and one or more noise component signals;
wherein the step of reentering the outputs of the blind adaptive filter into the singular value decomposition to undergo another round of separation comprises the steps of:
determining one or more blind separators based on singular value decomposition; and
employing the one or more blind separators to separate the one or more fetal heart component signals from the one or more maternal heart component signals and the one or more noise component signals.

19. An apparatus, comprising:
one or more processor components that separate one or more fetal heart component signals from heart signal information obtained from a pregnant female based on singular value decomposition;
wherein one or more of the one or in ore processor components compute a singular value decomposition of a covariance matrix of the heart signal information to yield a set of output signals;
wherein the one or more of the one or more processor components compute a delay parameter to minimize an absolute value of cross-correlations between the set of output signals;
wherein the one or more of the one or more processor components take a singular value decomposition of the sum of a covariance matrix of the set of output signals; and
wherein the one or more of the one or more processor components take a singular value decomposition of a transpose of the covariance matrix of the set of output signals to yield a separated output estimate of the one or more fetal heart component signals.

20. The apparatus of claim 19, wherein the one or more of the one or more processor components employ one or more analog-to-digital converters to digitize the heart signal information in preparation for execution of one or more signal processing procedures by the one or more of the one or more processor components.

21. The apparatus of claim 20, wherein the one or more signal processing procedures comprise one or more filtering procedures;

wherein the one or more of the one or more processor components employ the one or more analog-to-digital converters to digitize the heart signal information in preparation for execution of the one or more filtering procedures by the one or more of the one or more processor components;

wherein the one or more of the one or more processor components employ one or more non-linear filters and one or more non-linear inverse filters to reduce one or more amplitudes of one or more components of the heart signal information.

22. The apparatus of claim 20, wherein the one or more signal processing procedures comprise one or more filtering procedures;

wherein the one or more of the one or more processor components employ the one or more analog-to-digital converters to digitize the heart signal information in preparation for execution of the one or more filtering procedures by the one or more of the one or more processor components;

wherein the one or more of the one or more processor components employ one or more blind adaptive filters to reduce one or more amplitudes of the heart signal information.

23. The apparatus of claim 19, wherein the heart signal information comprises a plurality of electrocardiogram signals;

wherein the one or more of the one or more processor components record the plurality of electrocardiogram signals through employment of three or more electrode pairs of:
an abdominal electrode pair;
a chest electrode pair; and
a thoracic electrode pair.

24. The apparatus of claim 19, wherein the heart signal information comprises a plurality of magnetocardiogram signals;

wherein the one or more of the one or more processor components record the plurality of magnetocardiogram signals through employment of three or more sensors of:
an abdominal sensor;
a chest sensor; and
a thoracic sensor.

25. The apparatus of claim 19, wherein the one or more of the one or more processor components separate one or more of the one or more fetal heart component signals from the heart signal information based on singular value decomposition at any selected time at or after a twelfth week of pregnancy of the pregnant woman.

26. An article, comprising:
one or more computer-readable signal-bearing media; and
means in the one or more media for separating one or more fetal heart component signals from heart signal information obtained from a pregnant female based on singular value decomposition, wherein the means in the one or more media for separating one or more fetal heart component signals from the heart signal information obtained from the pregnant female based on singular value decomposition comprises:
means in the one or more media for computing a singular value decomposition of a covariance matrix of the heart signal information to yield a set of output signals;
means in the one or more media for computing a delay parameter to minimize an absolute value of cross-correlations between the set of output signals;
means in the one or more media for taking a singular value decomposition of the sum of a covariance matrix of the set of output signals; and
means in the one or more media for taking a singular value decomposition of a transpose of the covariance matrix of the set output signals to yield a separated output estimate of the one or more fetal heart component signals.

27. The article of claim 26, wherein the means in the one or more media for separating the one or more fetal heart component signals from the heart signal information obtained from the pregnant female based on singular value decomposition comprises means in the one or more media for employing a cepstral transformation, a cepstral filtration, and an inverse cepstral transformation to reduce the noise in the one or more fetal heart component signals;

wherein the means in the one or more media for separating the one or more fetal heart component signals from the heart signal information obtained from the pregnant female based on singular value decomposition comprises means in the one or more media for employing the cepstral transformation to identify one or more noise components in the one or more fetal heart component signals;

wherein the means in the one or more media for separating the one or more fetal heart component signals from the heart signal information obtained from the pregnant female based on singular value decomposition comprises means in the one or more media for employing the cepstral filtration to reduce one or more amplitudes of the one or more noise components in the one or more fetal heart component signals to change the one or more fetal heart component signals into one or more reduced noise fetal heart component signals;

wherein the means in the one or more media for separating the one or more fetal heart component signals from the heart signal information obtained from the pregnant female based on singular value decomposition comprises means in the one or more media for employing the inverse cepstral transformation to output one or more of the one or more reduced noise fetal heart component signals.

28. A method, comprising the steps of:
employing one or more filters to extract one or more fetal heart component signals from heart signal information obtained from pregnant female;
separating the one more fetal heart component signals from the heart signal information based on independent component analysis; and
employing one or more blind adaptive filtering components to reduce noise in the one or more fetal heart component signals wherein the step of employing one or more blind adaptive filtering components to reduce noise in the one or more fetal heart component signals comprises the step of:
operating the one or more blind adaptive filtering components in one or more of a frequency domain, a cepstral domain, and/or a wavelet transform domain, wherein the one or more blind adaptive filtering components operate in the cepstral domain, wherein the step of employing the cepstral analysis to reduce noise in the one or more fetal heart component signals comprises the steps of:
employing a cepstral transformation, a cepstral filtration, and an inverse cepstral transformation to reduce the noise in the one or more fetal heart component signals;
employing the cepstral transformation to identify one or more noise components in the one or more fetal heart component signals;

employing the cepstral filtration to reduce one or more amplitudes of the one or more noise components in the one or more fetal heart component signals to change the one or more fetal heart component signals into one or more reduced noise fetal heart component signals; and employing the inverse cepstral transformation to output one or more of the one or more reduced noise fetal heart component signals.

29. The method of claim 28, wherein the one or more filters comprise a non-linear filter and a non-linear inverse filter, wherein the step of employing the one or more filters to extract the one or more fetal heart component signals from the heart signal information obtained from the pregnant female comprises the steps of:

employing the non-linear filter and the non-linear inverse filter to reduce one or more amplitudes of the heart signal information obtained from the pregnant female; and employing one or more analog-to-digital converters to digitize the heart signal information upon receipt of the heart signal information.

30. The method of claim 28, wherein the heart signal information comprises the one or more fetal heart component signals, one or more maternal heart component signals, and one or more noise component signals, wherein the step of separating the one or more fetal heart component signals from the heart signal information obtained from the pregnant female based on independent component analysis comprises the steps of:

employing one or more analog-to-digital converters to digitize the heart signal information upon receipt of the heart signal information;

employing one or more non-linear filters and one or more non-linear inverse filters to reduce one or more amplitudes of the heart signal information;

employing independent component analysis to separate the one or more fetal heart component signals from the one or more maternal heart component signals and the one or more noise component signals;

employing one or more cepstral transformation components to identify one or more noise components in the one or more fetal heart component signals;

reducing one or more amplitudes of the one or more noise components in the one or more fetal heart component signals to change the one or more fetal heart component signals into one or more reduced noise fetal heart component signals; and employing one or more inverse cepstral transformation components to output one or more of the one or more reduced noise fetal heart component signals.

31. An apparatus, comprising:

one or more processor components that cause one or more filters to extract one or more fetal heart component from heart signal information obtained from a pregnant female;

wherein a first one or more of the one or more processor components separate the one or more fetal heart component signals from the heart signal information based on independent component analysis;

wherein a second one or more of the one or more processor components employ one or more blind adaptive filtering components to reduce noise in the one or more fetal heart component signals, wherein the second one or more of the one or more processor components employ cepstral transformation to identify one or more noise components in the one or more fetal heart component signals;

wherein the second one or more of the one or more processor components employ cepstral filtration to reduce one or more amplitudes of the one or more noise components in the one or more fetal heart component signals to change the one or more fetal heart component signals into one or more reduced noise fetal heart component signals;

wherein the second one or more of the one or more processor components employ inverse cepstral transformation to output one or more of the one or more reduced noise fetal heart component signals.

32. The apparatus of claim 31, wherein the one or more filters comprise a non-linear filter and a non-linear inverse filter;

wherein a third one or more of the one or more processor components cause the non-linear filter and the non-linear inverse filter to reduce one or more amplitudes of the heart signal information obtained from the pregnant female.

33. The apparatus of claim 31, wherein the heart signal information comprises a plurality of electrocardiogram signals;

wherein a third one or more of the one or more processor components record the plurality of electrocardiogram signals through employment of three or more electrode pairs of:

an abdominal electrode pair;

a chest electrode pair; and a thoracic electrode pair.

34. The apparatus of claim 31, wherein the heart signal information comprises a plurality of magnetocardiogram signals;

wherein a third one or more of the one or more processor components record the plurality of magnetocardiogram signals through employment of three or more sensors of:

an abdominal sensor;

a chest sensor: and a thoracic sensor.

35. The apparatus of claim 31, wherein the one or more blind adaptive filtering components operate in one or more of a frequency domain, a cepstral domain, and/or a wavelet transform domain.

36. An article, comprising:

one or more computer-readable signal-bearing media;

means in the one or more media for employing one or more filters to extract one or more fetal heart component signals from heart signal information obtained from a pregnant female;

means in the one or more media for separating the one or more fetal heart component signals from the heart signal information based on independent component analysis; and means in the one or more media for employing a cepstral analysis to reduce noise in the one or more fetal heart component signals.

37. The article of claim 36, wherein the means in the one or more media for employing the cepstral analysis to reduce noise in the one or more fetal heart component signals comprises means in the one or more media for employing a cepstral transformation, a cepstral filtration, and an inverse cepstral transformation to reduce the noise in the one or more fetal heart component signals;

wherein the means in the one or more media for employing the cepstral analysis to reduce noise in the one or more fetal heart component signals comprises means in the one or more media for employing the cepstral transformation to identify one or more noise components in the one or more fetal heart component signals;

wherein the means in the one or more media for employing the cepstral analysis to reduce noise in the one or more fetal heart component signals comprises means in the one or more media for employing the cepstral filtration to reduce one or more amplitudes of the one or more noise components in the one or more fetal heart component signals to change the one or more fetal heart component signals into one or more reduced noise fetal heart component signals;

wherein the means in the one or more media for employing the cepstral analysis to reduce noise in the one or more fetal heart component signals comprises means in the one or more media for employing the inverse cepstral transformation to output one or more of the one or more reduced noise fetal heart component signals.

* * * * *